(12) United States Patent
Kishishita et al.

(10) Patent No.: US 6,346,642 B1
(45) Date of Patent: Feb. 12, 2002

(54) MIXED CRYSTALS COMPRISING ASPARTAME AND ASPARTAME DERIVATIVE AND PROCESS FOR PRODUCING THE SAME

(75) Inventors: Akihiro Kishishita; Kazutaka Nagashima, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/591,562

(22) Filed: Jun. 13, 2000

Related U.S. Application Data

(63) Continuation of application No. PCT/JP98/05532, filed on Dec. 7, 1998.

(30) Foreign Application Priority Data

Dec. 15, 1997 (JP) .............................................. 9-344777

(51) Int. Cl.[7] ............................................ C07C 229/00
(52) U.S. Cl. ......................................... 560/41; 560/40
(58) Field of Search ..................................... 560/40, 41

(56) References Cited

U.S. PATENT DOCUMENTS 5,041,607 A * 8/1991 Naruse et al.
5,480,668 A   1/1996 Nofre et al.
5,510,508 A * 4/1996 Claude et al.
5,728,862 A * 3/1998 Prakash et al.

FOREIGN PATENT DOCUMENTS

JP    8-503206    4/1996

OTHER PUBLICATIONS

Derwent abstract (Acc No. 1998–506404) of WO 9839979. Ishii et al. (1998). Sweetener composition with improved and balanced sweetness.*
Derwent abstract (Acc No. 2000–053011) of WO 9957998. Hirano et al. (1999). Aspartame sweetener composition for foodstuffs, drinks and pharmaceuticals.*

* cited by examiner

*Primary Examiner*—Paul J. Killos
*Assistant Examiner*—Mahreen Chaudhry
(74) *Attorney, Agent, or Firm*—Oblon, Spivak, McClelland, Maier & Neustadt, P.C.

(57) ABSTRACT

There is provided a novel mixed crystal comprising aspartame (APM) and N-[N-(3,3-dimethylbutyl)-L-α-aspartyl]-L-phenylalanine methyl ester, which can be used as a sweetener having considerably improved quality of sweetness, etc.

The above mixed crystal can be easily produced industrially by subjecting a solution containing the above-mentioned APM and APM derivative to a crystallizing operation followed by the separation of the mixed crystal thus precipitated.

15 Claims, No Drawings

US 6,346,642 B1

MIXED CRYSTALS COMPRISING ASPARTAME AND ASPARTAME DERIVATIVE AND PROCESS FOR PRODUCING THE SAME

The present application is a continuation application of PCT/JP98/05532 filed Dec. 7, 1998 which claims priority to JP 9-344777 filed Dec. 12, 1998.

TECHNICAL FIELD OF INVENTION

The present invention relates to a novel mixed crystal comprising the sweetening substances of aspartame (APM) and N-[N-(3,3-dimethylbutyl)-L-α-aspartyl]-L-phenylalanine methyl ester, which hereinafter may be abbreviated to "N-(3,3-dimethylbutyl)-APM" and simply referred to as "APM derivative", and a process for production thereof.

BACKGROUND OF ART

In recent years, as eating habits have been improved to a high level, fatness caused by excessive sugar intake and diseases accompanied by fatness have been at issue. Accordingly, the development of a low-calory sweetening agent (sweetener) that replaces sugar has been in demand. The aspartame (APM) which is excellent in safety and quality of sweetness, is widely used as a sweetening agent. However, this is somewhat problematic in stability.

Under these circumstances, in the French Patent No.2697844 specification, it is stated that derivatives in which an alkyl group is introduced on an amino group of aspartic acid constituting the APM are studied in one approach to improve slightly the stability and to improve the sweetening potency, and among them and N-(3,3-dimethylbutyl)-APM is markedly improved in the sweetening potency. For the production of N-(3,3-dimethylbutyl)-APM, a process for alkylating APM reductively under the coexistence of 3,3-dimethylbutylaldehyde with sodium cyanoborohydride in methanol (refer to FR 2697844 specification), and a process for alkylating APM reductively under the coexistence of 3,3-dimethylbutylaldehyde with platinum carbon as the catalyst in a mixed solvent of water and methanol at a pH value in a range of 4.5 to 5 (refer to the above-mentioned WO95/30689 specification) are known.

The sweetening potencies of N-(3,3-dimethylbutyl)-APM being a sweetener having sweetness in a high degree and APM being an amino acid based sweetener, are reported to be 10,000 times by weight ratio (refer to Japanese Patent Kohyou Publication JP-A-8-503206) and about 200 times by weight ratio (refer to Japanese Patent Kokoku Publication JP-B-47-31031) that of sucrose, respectively.

The properties in quality of sweetness for N-(3,3-dimethylbutyl)-APM are not reported in details, and however such compound is extremely weak in early taste (which means that a sweetener when put in the mouth tastes sweet as early as sucrose), and extremely strong in later taste (which means that a sweetener tastes sweet later than sucrose), according to the present inventors, findings. It is strong in astringency (astringent taste) and badly-balanced for quality of sweetness as compared to sucrose. On the other hand, with respect to APM, its properties for quality of sweetness is weak in early taste, and strong in later taste, although they are not so bad as those in N-(3,3-dimethylbuty)-APM. Therefore, any one of both compounds has the properties for quality of sweetness which is weak in early taste, and strong in later taste, and thus is out of quality of sweetness, taking into account the fact that sucrose is natural in sweetness.

With respect to improvement in the properties for quality of sweetness, there are various proposals for improvement mainly in later taste (For example, refer to Japanese Patent Kokai Publication JP-A-56-148255, JP-A-58-141760, JP-A-58-220668, etc.). Methods for obtaining a natural quality of sweetness closer to that in sucrose, for example, by the combination with sucrose (refer to Japanese Patent Kokai Publication JP-A-57-152862), etc. are found among the proposals. On the other hand, it is possible that early taste is intensified, later taste is weakened, and also intringency is weakened to take a good balance in quality of sweetness by combining homogeneously and properly N-(3,3-dimethylbutyl)-APM being a sweetener having sweetness in a high degree with APM being an amino acid based sweetener, according to the findings found by the inventors in the present invention. For example, by combining homogeneously and properly N-(3,3-dimethylbutyl)-APM which is weak in early taste with APM, it is improved in early taste and thereby is expected to give a sweetener having sweetness in a high degree and quality of sweetness totally good in balance, closer to that of sucrose, as compared to N-(3, 3-dimethylbutyl)-APM or APM each alone.

The sweetening potency of N-(3,3-dimethylbutyl)-APM is 10,000 times by weight ratio (refer to Japanese Patent Kohyou Publication JP-A-8-503206) as much as that of sucrose, and therefore it is problematic in adjusting a degree of sweetness while using it. Accordingly, a combination of N-(3,3-dimethylbutyl)-APM with APM which is proper for sweeteners is expected in view of not only improvement in quality of sweetness, but also uses thereof. Under these circumstances, it may be considered that an improvement in quality of sweetness, etc. based on these proper combinations is a problem to be solved at present.

OBJECT OF INVENTION

An object of the present invention is, in considering the properties in quality of sweetness present in APM and N-(3,3-dimethylbutyl)-APM described in the previous section, to provide an appropriate combination of APM with N-(3,3-dimethylbutyl)-APM which is improved in quality of sweetness, etc. and thereby to solve the above-mentioned problem.

DISCLOSURE OF INVENTION

In order to solve the problem and achieve the object of the present invention, the present inventors have studied earnestly and found the fact that a novel mixed crystal comprising N-(3,3-dimethylbutyl)-APM and aspartame (APM) can be obtained by subjecting a solution containing N-(3,3-dimethylbutyl)-APM and APM to crystallization, and further that thus obtained mixed crystal can achieve the above-mentioned object, is homogeneous and can improve considerably quality of sweetness, etc., in different from a simple mixture of both (two kinds of) crystals, each obtained separately from the 2 compounds.

The powder X-ray diffraction pattern for the crystal (CuKα-ray; and so forth) is the same pattern to that for APM alone (For example, in the wet crystal thereof it is a crystal in IA type, and in the dry crystal thereof it is a crystal in IB type, as seen from the Japanese Patent Kokoku Publication JP-B-6-31312.). However, in the analysis of the high performance liquid chromatography, N-(3,3-dimethylbutyl)-APM is detected. On the other hand, in the case of a mixture wherein the crystals of N-(3,3-dimethylbutyl)-APM and the crystals of APM are simply mixed, peaks based on the both crystals of 2 compounds are found in the powder X-ray diffraction pattern therefor. However, from the facts that N-(3,3-dimethylbutyl)-APM is detected in the analysis of the high performance liquid chromatography, although the powder X-ray diffraction pattern therefor is the same pattern to that for APM alone, it has been found that the obtained crystal mentioned above is a novel mixed crystal comprising N-(3,3-dimethylbutyl)-APM and APM.

Further, it has been found that a novel mixed crystal comprising APM and N-(3,3-dimethylbutyl)-APM can be easily obtained by subjecting a solution containing APM and N-(3,3-dimethylbutyl)-APM to crystallization in a crystallizing operation followed by the separation of the crystals precipitated.

Based on these findings, the present invention has been completed.

That is to say, the present invention is directed to a novel mixed crystal comprising at least N-(3,3-dimethylbutyl)-APM and APM, and also to a process for producing a novel mixed crystal comprising at least N-(3,3-dimethylbutyl)-APM and APM, which comprises: subjecting a solution containing said 2 types of the compounds to a crystallizing operation.

Further, the present invention contains the followings:

1. The above mixed crystal, wherein said APM and said APM derivative is contained in a weight ratio of APM to said APM derivative being about 100 to 0.1–10, and preferably about 100 to 0.3–3 for a sweetener.

The crystals containing the mixed crystal or the crystals made of the mixed crystal under these ranges can be easily produced by selecting properly a condition for crystallization thereof when producing the same, as described later.

2. The above process for production of the mixed crystal, wherein a solvent used in said crystallizing operation is a water or an alcohol alone selected from water and alcohols, or a mixed solvent containing more than one solvents optionally mixed, and selected from the group consisting of these plural alcohols and water.

3. The above process, wherein said alcohols are ethyl alcohol and methyl alcohol.

4. The above process, wherein a ratio of APM to N-(3,3-dimethylbutyl)-APM at the initial concentration contained in the solution for said crystallizing operation is 4 or more (not less than 4), preferably in particular 10 or more (not less than 10) by weight.

5. The above process, wherein said crystallizing operation comprises the steps of: adjusting (setting) an initial concentration (APM) of the solution for crystallization so that APM may be exist in about 10 grams or more (not less than about 10 grams), preferably in particular about 20 to 100 grams per 1 liter of solvent present in the solution containing APM which should be precipitated after cooling the solution, and cooling the solution through heat transfer by conduction without giving a flowing or movement by force such as a mechanical stirring or the like thereto so that a pseudo-solid phase like an ice-confection or an ice-sweet (sherbet) may be produced in an entire solution from appearances, to form the pseudo-solid phase.

6. A sweetener comprising the above mixed crystal, or comprising the above mixed crystal and a carrier usable for sweeteners, as needed, and a process for imparting sweetness, comprising the step of: using the mixed crystal for a material requesting sweetness, such as foods, cosmetics in the mouth (dental rinse, mouth wash, etc.), oral pharmaceutical products for animals like humans, etc.

EMBODIMENTS OF INVENTION

The novel mixed crystal in the present invention can be used as an excellent sweetener, as explained above, and when the crystal is produced, known methods for crystallization as such is applied and carried out for the crystallizing operation (step) employed in the present invention.

That is to say, on production of the mixed crystal comprising N-(3,3-dimethylbutyl)-APM and APM, by subjecting a material containing such 2 kinds of compounds in the form of solution to the crystallizing operation for crystallization and separating thus precipitated mixed crystal, a mixed crystal comprising N-(3,3-dimethylbutyl)-APM and APM can be easily produced.

For the solvent employed in the crystallizing operation, a suitable solvent may be selected for the crystallization by studying or considering a solubility thereof for the both compounds.

For the solvent, for example, one solvent selected from water, ethyl acetate, methyl acetate, acetic acid, toluene, hexane, tetrahydrofuran, acetonitrile, dimethoxyethane, ethyl ether, isopropyl alcohol, ethyl alcohol, methyl alcohol, dichloromethane, chloroform and 1,2-dichiloroethane and the like, and a mixed solvent containing 2 or more solvents selected from these above solvents may be enumerated.

In case that there may be a material or serious problem or question as to the solvent remaining in the end product in view of quality of the product, a water or a mixed solvent of water and alcohol-based solvent(s), such as ethyl alcohol, methyl alcohol and the like may be preferably employed.

For the starting material employed in the crystallizing operation, i.e., a solution containing N-(3,3-dimethylbutyl)-APM and APM, any solution containing at least said 2 kinds of compounds may be employed, and therefore, a slurry or a solution thereof obtained in a course of production for the each compound may be mixed therewith and may be used for the starting material, and also a slurry or a solution containing N-(3,3-dimethylbutyl)-APM and APM obtained in the course of production for the N-(3,3-dimethylbutyl)-APM may be employed.

Thus obtained solution may be subjected to usual or conventional crystallizing operation for the crystallization, such as crystallization by cooling, crystallization by concentration, crystallization by neutralization, etc. to obtain the mixed crystal of APM and N-(3,3-dimethylbutyl)-APM. In case that there is much APM therein, since it is known that minute or refined crystals may be formed under stirring the solution, it is preferable to subject the solution to crystallization under standing (static crystallization) or to crystallization under stirring, if required, after the crystallization under standing, in order to restrain a formation of minute crystals. On crystallization thereof under standing (static crystallization), the method for adjusting (setting) or controlling an initial concentration of the solution for crystallization so that APM therein may exist in about 10 grams or more, preferably about 20 to 100 grams per 1 liter of the solvent present in the solution containing APM which may be precipitated when cooling the solution, and cooling the solution through conductive heat transfer by conduction without giving the flowing or movement by force such as mechanical stirring or the like thereto so that a pseudo-solid phase like an ice-confection or an ice-sweet (sherbet) may be produced in an entire solution from appearances, to form the pseudo-solid phase, as described in, for example, Japanese Patent Kokoku Publication JP-B-03-025438, may be employed.

For the initial concentrations of APM and N-(3,3-dimethylbutyl)-APM in the solution subjected to the crystallizing operation, when a ratio of APM to N-(3,3-dimethylbutyl)-APM may not be 4 or more by weight, a complete mixed crystal does not form. The ratio of APM to N-(3,3-dimethylbutyl)-APM to be employed preferably, may be not less than 4, more preferably not less than 10 by weight.

For a good point (advantage) of the mixed crystal, naturally, the fact that a homogeneously mixed form is achieved as mentioned, can be given, as compared to the case of a mixture obtained by mixing crystals of N-(3,3-dimethylbutyl)-APM with crystals of APM, each separately produced.

In relation to the sherbet or the slurry obtained in the crystallization, the end product can be obtained by subjecting the same to separation of a solid material from a liquid, drying the solid material, and further granulating them, if required.

For the methods for separation of a solid material from a liquid, a filtration and a centrifugation are exemplified, for the methods of dryness, methods with a vacuum drier, a fluidized-bed dryer, a spray dryer, a micron dryer and the like are exemplified, and for the methods for granulation, a dry granulating, a wet granulating and the like are exemplified. However, they are not limited to those exemplified.

There is no difficulty, when the mixed crystal obtained in the present invention may be used for a sweetener or production thereof. For example, it can be easily conducted by applying known methods for production of sweeteners or for use thereof in such case.

PREFERRED EMBODIMENTS

The present invention is further illustrated specifically by referring to the following examples and comparative example.

EXAMPLE 1

APM (15.6 g, 0.051 mol) in the water content of 3.9% by weight and N-(3,3-dimethylbutyl)-APM (0.06 g, 0.15 mmol) in the water content of 5.5% by weight were added to water (300 ml) and heated at 70° C. for 1 hour to be dissolved. Accordingly, APM and N-(3,3-dimethylbutyl)-APM thus dissolved in the solution were in the concentrations of 5.2 g and 0.02 g per 100 ml of the solution, respectively, and in the ratio of APM to N-(3,3-dimethylbutyl)-APM being 260 in the initial concentration. Thus obtained solution was subjected to crystallization at 5° C. for 3 hours while standing to prepare a sherbet (a sherbet-like material. The sherbet was stirred overnight to a slurry and was subjected to resolution of super saturation. Thus obtained slurry was filtrated through a filter paper of 1 μm to separate wet crystals from the mother liquor. The wet crystals were dried under reduced pressure at 50° C. overnight to obtain 13.2 g of the dried crystals in the water content of 3.4% by weight (APM: 97.4 weight %; N-(3,3-dimethylbutyl)-APM: 0.2 weight % in the determination by the high performance liquid chromatography). In the powder X-ray diffraction pattern (CuK α-ray) thereof, the pattern showed one for a crystal in the IB type.

EXAMPLES 2 to 11

The aqueous solutions containing APM and N-(3,3-dimethylbutyl)-APM described in the table 1 were subjected to crystallization in the crystallizing operation. The compositions of solution for crystallization and the compositions of the dried crystals obtained were shown in the table 1. Any dried crystal in the crystals thus obtained was in the form of the mixed crystal.

TABLE 1

Compositions of Solution for Crystallization and Compositions of Dried Crystals Obtained:

| Example No. | Concentration of Solution for Crystallization [g/dl] | | Ratio of APM to N-(3,3-dimethylbutyl)-APM in Initial Concentration | Composition of Dried Crystals [weight %] | | |
|---|---|---|---|---|---|---|
| | APM | N-(3,3-dimethyl-butyl)-APM | | APM | N-(3,3-dimethyl-butyl)-APM | Water |
| 2 | 4.87 | 0.05 | 97 | 93.1 | 0.6 | 2.9 |
| 3 | 4.74 | 0.09 | 53 | 92.8 | 1.0 | 3.6 |
| 4 | 5.05 | 0.50 | 10 | 87.7 | 4.7 | 3.8 |
| 5 | 4.99 | 0.98 | 5 | 90.4 | 7.3 | 3.0 |
| 6 | 5.08 | 1.31 | 4 | 87.5 | 9.5 | 3.4 |
| 7 | 4.17 | 0.05 | 83 | 95.4 | 0.7 | 3.1 |
| 8 | 4.15 | 0.10 | 42 | 93.8 | 1.4 | 3.0 |
| 9 | 3.63 | 0.04 | 91 | 97.3 | 0.8 | 2.9 |
| 10 | 3.54 | 0.10 | 35 | 93.3 | 1.6 | 2.9 |
| 11 | 2.07 | 0.05 | 41 | 94.7 | 1.4 | 3.5 |
| 12 | 2.06 | 0.10 | 21 | 92.3 | 2.0 | 3.8 |

Comparative Example 1

APM (5.31 g, 0.017 mol) in the water content of 3.9% by weight and N-(3,3-dimethylbutyl)-APM (1.76 g, 4 mmol) in the water content of 5.5% by weight were added to water (100 ml) and heated at 70° C. for 1 hour to be dissolved. Accordingly, APM and N-(3,3-dimethylbutyl)-APM thus dissolved in the solution were in the concentrations of 5.1 g and 1.7 g per 100 ml of the solution, respectively, and in the ratio of APM to N-(3,3-dimethylbutyl)-APM being 3 in the initial concentration. Thus obtained solution was subjected to crystallization at 5° C. overnight while standing to resolve super saturation. Thus obtained crystals were filtrated through a filter paper of 1 μm to separate wet crystals from the mother liquor. The wet crystals were dried under reduced pressure at 50° C. overnight to obtain 13.2 g of the dried crystals in the water content of 6.75% by weight (APM: 80.0 weight %; N-(3,3-dimethylbutyl)-APM: 9.0 weight % in the determination of the high performance liquid chromatography). In the powder X-ray diffraction pattern (CuK α-ray) thereof, the pattern did not show one for a crystal in the IB type.

EFFECTS OF INVENTION

The novel mixed crystal comprising N-(3,3-dimethylbutyl)-APM and APM obtained in the present invention, can be used as a sweetener having considerably improved quality of sweetness, etc., and also can provide a homogeneous and high quality sweetener in comparison with that obtained by producing crystals of N-(3,3-dimethylbutyl)-APM and crystals of APM, each separately, and mixing two kinds of the separately produced crystals.

The novel mixed crystal in the present invention can be easily produced industrially by subjecting a solution containing two kinds of the above-mentioned compounds to a conventional crystallizing operation followed by the separation of the mixed crystal thus precipitated.

What is claimed is:
1. A mixed crystal comprising N-[N-(3,3-dimethylbutyl)-L-α-aspartyl]-L-phenylalanine methyl ester and APM.
2. The mixed crystal of claim 1, wherein the ratio of said APM to N-[N-(3,3-dimethylbutyl)-L-α-aspartyl]-L-phenylalanine methyl ester is 100 to from 0.1 to 10 by weight.

3. The mixed crystal of claim 1, wherein the ratio of said APM to N-[N-(3,3-dimethylbutyl)-L-a-aspartyl]-L-phenylalanine methyl ester is 100 to from 0.3 to 3 by weight.

4. A sweetener comprising the mixed crystal of claim 2 and carrier.

5. A process for producing a mixed crystal comprising APM and N-[N-(3,3-dimethylbutyl)-L-α-aspartyl]-L-phenylalanine methyl ester wherein the process comprises crystallizing a solution comprising APM and N-[N-(3,3-dimethylbutyl)-L-α-aspartyl]-L-phenylalanine methyl ester, wherein said APM is present in said solution in an amount which is four or more times by weight than the amount of N-[N-(3,3-dimethylbutyl)-L-α-aspartyl]-L-phenylalanine methyl ester in said solution.

6. The process of claim 5, wherein said crystallizing comprises crystallizing in water, alcohol or a mixture of water and alcohol.

7. The process of claim 5, wherein the alcohol is ethyl alcohol, methyl alcohol, or a mixture thereof.

8. The process of claim 5, wherein the crystallizing comprises adjusting the concentration of the APM in the solution to at least 10 grams per liter.

9. The process of claim 5, wherein the crystallizing comprises cooling the solution with conductive heat transfer.

10. The process of claim 5, wherein said APM is present in said solution in an amount which is ten or more times by weight than the amount of N-[N-(3,3-dimethylbutyl)-L-a-aspartyl]-L-phenylalanine methyl ester in said solution.

11. The process of claim 5, wherein said APM is present in said solution in an amount greater than 20 to 100 grams per liter.

12. A process for producing a mixed crystal comprising APM and N-[N-(3,3-dimethylbutyl)-L-α-aspartyl]-L-phenylalanine methyl ester wherein the process comprises preparing a solution comprising APM and N-[N-(3,3-dimethylbutyl)-L-α-aspartyl]-L-phenylalanine methyl ester, wherein said APM is present in said solution in an amount greater than 10 grams per liter, and wherein said APM is present in said solution in an amount which is four or more times by weight than the amount of N-[N-(3,3-dimethylbutyl)-L-α-aspartyl]-L-phenylalanine methyl ester in said solution;

cooling the solution with conductive heat transfer to produce a pseudo-solid phase, wherein the APM and N-[N-(3,3-dimethylbutyl)-L-α-aspartyl]-L-phenylalanine methyl ester are precipitated.

13. The process of claim 12, wherein said conductive heat transfer comprises mechanical stirring.

14. The process of claim 12, wherein said APM is present in said solution in an amount which is ten or more times by weight than the amount of N-[N-(3,3-dimethylbutyl)-L-a-aspartyl]-L-phenylalanine methyl ester in said solution.

15. The process of claim 12, wherein said APM is present in said solution in an amount greater than 20 to 100 grams per liter.

* * * * *